(12) United States Patent
Farbarik

(10) Patent No.: US 7,891,354 B2
(45) Date of Patent: Feb. 22, 2011

(54) SYSTEMS AND METHODS FOR PROVIDING ACTIVE NOISE CONTROL IN A BREATHING ASSISTANCE SYSTEM

(75) Inventor: John M. Farbarik, Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 989 days.

(21) Appl. No.: 11/537,526

(22) Filed: Sep. 29, 2006

(65) Prior Publication Data

US 2008/0110459 A1    May 15, 2008

(51) Int. Cl.
*F16K 31/02* (2006.01)

(52) U.S. Cl. .................. 128/204.21; 128/200.24; 128/204.18; 381/71.1

(58) Field of Classification Search ............ 128/200.24, 128/204.18, 204.21, 204.23; 381/71.1–71.14
See application file for complete search history.

(56) References Cited

U.S. PATENT DOCUMENTS

| | | | |
|---|---|---|---|
| 4,538,297 A | 8/1985 | Waller, Jr. ..................... | 381/94 |
| 4,654,871 A * | 3/1987 | Chaplin et al. ................ | 381/72 |
| 4,697,593 A * | 10/1987 | Evans et al. .................. | 600/343 |
| 5,321,759 A * | 6/1994 | Yuan .......................... | 381/71.9 |
| 6,259,792 B1 | 7/2001 | Lambrecht ................. | 381/73.1 |
| 6,418,227 B1 * | 7/2002 | Kuo ........................ | 381/71.11 |
| 6,480,821 B2 | 11/2002 | Macho et al. ............... | 704/207 |
| 7,448,382 B1 * | 11/2008 | Alexander et al. ..... | 128/204.18 |
| 2005/0115561 A1 | 6/2005 | Stahman | |
| 2005/0226435 A1 | 10/2005 | Steer ........................ | 381/71.7 |

FOREIGN PATENT DOCUMENTS

| | | |
|---|---|---|
| EP | 1228779 | 8/2002 |
| WO | 2005013879 A | 2/2005 |
| WO | WO2005016217 | 2/2005 |
| WO | WO2007040755 | 4/2007 |

(Continued)

OTHER PUBLICATIONS

Minogue et al., "Adaptively Cancelling Server Fan Noise", Analog Dialogue, http://www.analog.com/library/analogDialogue/archives/34-02/noise/index.html, 13 pages, Aug. 7, 2006.

(Continued)

*Primary Examiner*—Justine R Yu
*Assistant Examiner*—Valerie Skorupa

(57) ABSTRACT

A breathing assistance system having active noise control may include a gas delivery system, a patient interface, a connection system, and a noise control system. The gas delivery system may supply breathing gas to a patient via the connection system and the patient interface. The noise control system may include a processor, a speaker, a reference signal source, and a feedback sensor. The processor may generate noise control signals to be output by the speaker for canceling noise caused by a noise source of the breathing assistance system. The reference signal source may communicate reference signals associated with the noise source. The feedback sensor may detect noise caused by the noise source and noise control signals output by the speaker, and communicate to the processor feedback noise signals based on the detected noise. The processor may generate the noise control signals based at least on the reference signals and the feedback noise signals.

23 Claims, 5 Drawing Sheets

FOREIGN PATENT DOCUMENTS

WO     WO2007076570     7/2007

OTHER PUBLICATIONS

Denenberg, "Noise Cancellation: Quieting the Environment", http://doctord.dyndns.org:8000/Pubs/POTENT.htm, 13 pages, Aug. 7, 2006.

International Search Report and Written Opinion of International Searching Authority PCT/US2007/079683, 11 pages, Jan. 30, 2008.

International Search Report with Written Opinion PCT/US2007/079705, 10 pages, mailed May 2, 2008.

\* cited by examiner

SYSTEMS AND METHODS FOR PROVIDING ACTIVE NOISE CONTROL IN A BREATHING ASSISTANCE SYSTEM

TECHNICAL FIELD

The present disclosure relates generally to noise control and, more particularly, to systems and methods for providing active noise control in a breathing assistance system, such as a ventilator or CPAP device, for example.

BACKGROUND

A mechanical ventilator delivers air to a patient via tubing called a breathing circuit, and in some cases mixes additional oxygen into the air before being delivered to the patient. The gas delivered to the patient from the ventilator may be humidified and heated in the breathing circuit before it goes to the patient. The ventilator increases the pressure in the breathing circuit so that the air is pushed into the lungs for inspiration, and reduces the pressure so that the air in the lungs can be expired and vented to the atmosphere. Typically, one or more ventilator parameters may be determined and adjusted prior to attachment and during operation on the patient, including the mode of ventilation (e.g., CMV (controlled mandatory ventilation), SIMV (synchronized intermittent mandatory ventilation), or CPAP (constant positive airway pressure)); the patient's tidal volume (the volume of air inspired with each breath); the respiratory rate (the number of breaths per minute (BPM)); and the $O_2$ concentration, flow rate, airway pressure, and minute volume (the volume inspired and expired in one minute) of gas delivered to the patient.

Some ventilators generate noise during operation, which may be undesirable to the ventilator user or operator, particularly when the user is trying to sleep. For example, some breathing assistance systems include motors or other components that may produce a continuous noise, such as a humming, buzzing, or whining. In addition, the flow of air though a ventilator, particularly at high speed or high pressures, may produce undesirable noise.

SUMMARY

In accordance with one embodiment of the disclosure, a breathing assistance system having active noise control may include a gas delivery system, a patient interface, a connection system, and a noise control system. The gas delivery system may be operable to supply breathing gas. The patient interface may be configured to interface with a patient for delivering breathing gas to one or more breathing passages of the patient. The connection system may be configured to communicate breathing gas supplied by the gas delivery system to the patient interface for delivery to the patient. The noise control system configured to control noise caused by a noise source associated with the breathing assistance system, and may include a processor, a reference signal source, a speaker, and a feedback sensor. The processor may be configured to generate noise control signals for at least partially canceling noise caused by the noise source. The reference signal source may be configured to communicate to the processor reference signals associated with the noise source. The speaker may be operable to output the noise control signals generated by the processor for at least partially canceling noise caused by the noise source. The feedback sensor configured to detect noise caused by the noise source and noise control signals output by the speaker, and communicate to the processor feedback noise signals based on the detected noise. The processor may be configured to generate the noise control signals based at least on the reference signals and the feedback noise signals.

In accordance with another embodiment of the disclosure, a noise control system for controlling noise associated with a breathing assistance system includes a processor, a reference signal source, a speaker, and a feedback sensor. The processor may be configured to generate noise control signals for at least partially canceling noise caused by a noise source of a breathing assistance system. The reference signal source may be configured to communicate to the processor reference signals associated with the noise source. The speaker may be operable to output the noise control signals generated by the processor for at least partially canceling noise caused by the noise source. The feedback sensor configured to detect noise caused by the noise source and noise control signals output by the speaker, and communicate to the processor feedback noise signals based on the detected noise. The processor may be configured to generate the noise control signals based at least on the reference signals and the feedback noise signals.

In accordance with another embodiment of the disclosure, a system for providing active noise control in a breathing assistance system includes a gas delivery device, a sensor, a processor, and a speaker. The gas delivery device may be operable to supply pressurized gas for a breathing assistance system. The sensor may be operable to detect noise associated with the breathing assistance system, including noise caused by the gas delivery device. The processor may be operable to generate noise cancellation signals based at least on the detected noise, the noise cancellation signals operable to at least partially cancel the noise associated with the breathing assistance system. The speaker may be operable to output the generated noise control signals for at least partially reducing the noise caused associated with the breathing assistance system.

In accordance with another embodiment of the present disclosure, a method for controlling noise associated with a breathing assistance system may include using a first sensor to detect noise caused by a noise source of a breathing assistance system; communicating the detected noise as reference signals to a processor; using a speaker to output noise control signals for at least partially canceling the noise caused by the noise source; using a second sensor to detect (a) noise caused by the noise source and (b) noise control signals output by the speaker; communicating to the processor feedback signals based on the noise detected by the second sensor; and using the processor to generate noise control signals for output by the speaker based at least on the received reference signals and feedback signals.

In accordance with another embodiment of the disclosure, a breathing assistance system having active noise control may include gas delivery means, patient interfacing means, gas communication means, and noise controlling means. The gas delivery means may be configured for supplying breathing gas. The patient interfacing means may be configured for interfacing with a patient for delivering breathing gas to one or more breathing passages of the patient. The gas communication means may be configured for communicating breathing gas supplied by the gas delivery means to the patient interfacing means for delivery to the patient. The noise controlling means may be configured for controlling noise caused by a noise source associated with the breathing assistance system, and may include processing means, reference signal communication means, sound output means, and feedback communication means. The processing means may be configured for generating noise control signals for at least partially canceling noise caused by the noise source. The reference signal communication means may be configured for communicating to the processor reference signals associated with the noise source. The sound output means may be configured for outputting the noise control signals generated by the processor for at least partially canceling noise caused by the noise source. The feedback communication means may be configured for detecting noise caused by the noise source and noise control signals output by the speaker, and communicating to the processor feedback noise signals based on the detected noise. The processing means may generate the noise control signals based at least on the reference signals and the feedback noise signals.

BRIEF DESCRIPTION OF THE DRAWINGS

A more complete understanding of the present embodiments may be acquired by referring to the following description taken in conjunction with the accompanying drawings, in which like reference numbers indicate like features, and wherein.

DETAILED DESCRIPTION

Embodiments of the disclosure are best understood by reference to FIGS. 1 through 9, wherein like numbers are used to indicate like and corresponding parts.

Figure 1:
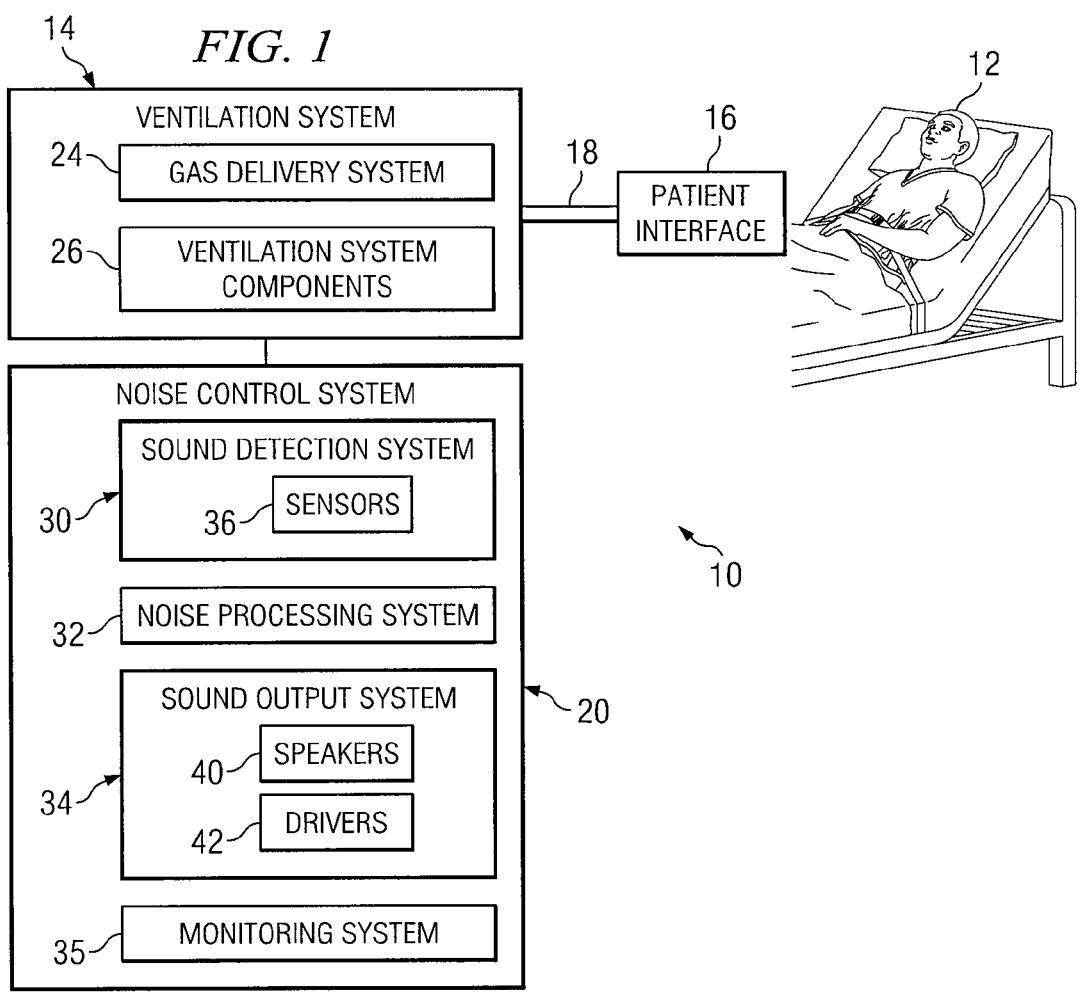
FIG. 1 illustrates a breathing assistance system providing active noise control functionality in accordance with one embodiment of the disclosure.

FIG. 1 illustrates a breathing assistance system 10 having active noise control functionality in accordance with one embodiment of the disclosure. In general, the active noise control functionality may actively control noise associated with the operation of breathing assistance system 10.

Generally, noise caused by breathing assistance system 10 may be dynamically detected and analyzed to generate noise control signals (or counter noise), which may then be output in order to control noise caused by breathing assistance system 10 that may be heard by the patient, an operator of system 10, or others within audible range. The noise may be detected in any suitable manner, such as using a microphone to detect audible noise and/or an accelerometer to detect vibrations associated with the noise. The noise control functionality may be at least partially active (i.e., dynamic), as opposed to fully-passive noise control techniques, such as insulation, for example. Such active, dynamic noise control may provide better noise control than fully-passive techniques. In addition, the active noise control system may be lighter and less space-consuming than passive systems, e.g., allowing for reduced weight and/or size of the breathing assistance system. In some embodiments, breathing assistance system 10 may also include passive noise control, such as using insulation and/or an insulating geometric configuration, for example.

As used herein, the term "noise" may refer to any audible sounds that may be associated with the operation of breathing assistance system 10, such as, but not limited to, noise caused by a motor (e.g., a blower motor), compressor, or other moving part(s), noise associated with gasses flowing though various channels within breathing assistance system 10 and/or through inlets and/or outlets of breathing assistance system 10, and/or noise associated with the vibration and/or other physical movement of any component of breathing assistance system 10, for example.

As used herein, the term "noise control" may include any type and/or extent of control, adjustment, or regulation of any noise parameter (e.g., tone, pitch, loudness (or amplitude or intensity), quality, and/or phase), such as full or partial noise reduction, cancellation, leveling, or smoothing, for example.

In some embodiments, breathing assistance system 10 may use one or more types of active noise control, including, for example:

(a) Detecting noise associated with breathing assistance system 10 and generating and outputting "noise cancellation signals" to at least partially reduce or cancel the noise associated with breathing assistance system 10; and (b) Detecting noise associated with breathing assistance system 10 and generating and outputting "noise leveling signals" to at least partially reduce variations in the sound output over time (i.e., to maintain a relatively constant sound output). Such technique may be used where noise associated with breathing assistance system 10 varies significantly over time, e.g., where a blower cycles between speeds for inhalation and exhalation phases. The noise leveling signals may sound similar to the noises produced by breathing assistance system 10 (e.g., noise generated by a motor), and may be added to such noises in order to provide a relatively constant total sound output from system 10. For example, in embodiments in which a motor speeds up (and thus generates more noise) during inhalation and speeds down (and thus generates less noise) during exhalation, noise leveling signals may be increased during exhalation and decreased during inhalation to provide a relatively constant total sound output over the complete breath.

Breathing Assistance System 10

As shown in FIG. 1, breathing assistance system 10 may be generally configured to provide breathing assistance (e.g., providing ventilation and/or treating an apnea or other breathing condition) to a patient 12. Breathing assistance system 10 may include a ventilation system 14, a patient interface 16, and a connection system 18 between ventilation system 14 and patient interface 16, and/or a noise control system 20 for controlling noise caused by breathing assistance system 10.

Ventilation system 14 may include any device or devices for providing breathing assistance to patient 12. For example, ventilation system 14 may comprise a ventilator, a respirator, a CPAP device, or BiPAP device. The term "gas" may refer to any one or more gases and/or vaporized substances suitable to be delivered to and/or from patient 12 via one or more breathing orifices (e.g., the nose and/or mouth), such as air, nitrogen, oxygen, any other component of air, $CO_2$, vaporized water, vaporized medicines, and/or any combination of two or more of the above, for example. The term "patient" may refer to any person or animal that is receiving breathing support from a ventilation system, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Ventilation system 14 may include a gas delivery system 24 and/or one or more other components 26 associated with providing breathing assistance to patient 12. Gas delivery system 24 may generally be operable to generate, supply, and/or deliver gas toward patient 12. For example, gas delivery system 24 may include a motorized blower operable to output pressurized gas, a piston-based compressor operable to output compressed gas, any other type of compressor, a tank and/or other container of pre-compressed gas, one or more valves for controlling the flow of gas from a gas source (e.g., a tank or a line in from the wall) toward patient 12, and/or any other suitable device or devices operable to generate and/or supply pressurized gas.

In certain embodiments, gas delivery system 24 may include one or more motorized blowers operable to deliver compressed gas toward patient 12. In some embodiments, the blower(s) may run at a relatively constant speed, and the pressure and/or flow rate of gas delivered toward patient 12 may be controlled by other means, e.g., one or more valves. In other embodiments, the speed of the blower(s) may be controlled in order to control the pressure and/or flow rate of gas delivered toward patient 12. In such embodiments, the noise caused by the motor-driven blower(s) may vary over time in relation to the speed of the blower(s). For example, for ventilation or bi-level CPAP therapy, the speed of a blower may be increased during the inhalation phase of each breath (thus increasing the noise caused by the blower), and decreased during the exhalation phase of each breath (thus decreasing the noise caused by the blower). Thus, the noise caused by the blower may be generally cyclical over time.

Components 26 may include any systems or devices associated with providing breathing assistance, e.g., any component or components of a ventilator, a CPAP device, a BiPAP device, or any other type of breathing assistance device. For example, components 26 may include one or more displays, user input devices or user interfaces, humidifiers, nebulizers, valves, conduits, processing devices, etc. One or more components 26 may generate noise that may be at least partially controlled by noise control system 20.

Patient interface 16 may include any device or apparatus for interfacing with patient 12 to deliver gas received from ventilation system 14 and connection system 18 to patient 12. For example, patient interface may include a mask (e.g., a nasal mask, a mouth mask, or a full face mask), one or more nasal pillows or cannulas leading into the nostrils, or a tracheal tube or catheter.

Connection system 18 may include any one or more conduits (e.g., one or more flexible hoses) for communicating gas from ventilation system 14 to patient interface 16. In some embodiments, connection system 18 may be referred to as a patient circuit or a breathing circuit.

Noise control system 20 may be generally operable to provide active noise control functionality (e.g., noise cancellation and/or noise leveling) to control noise caused by one or more components of system 10, e.g., to control the tone, pitch, loudness (or amplitude or intensity), quality, and/or phase of noise caused by system 10. Noise control system 20 may use any known or suitable techniques and/or algorithms for providing such active noise control. For example, noise control system 20 may use any known or suitable feedback and/or feedforward noise control techniques. Feedforward noise control techniques may refer, for example, to adaptive or dynamic equalization techniques.

In some embodiments, noise control system 20 may generate noise cancellation waves having the same or directly proportional amplitude and the opposite polarity (i.e., a reversed polarity waveform) as detected noise waves, which noise cancellation waves may be used to reduce the amplitude of (or otherwise reduce or cancel) the perceived noise. As another example (or in addition to polarity reversing techniques), noise control system 20 may use phase shifting (e.g., rotating frequencies 180 degrees out of phase) to generate noise cancellation waves. Any other known or suitable techniques may be used to generate for such noise cancellation or control.

Noise control system 20 may include any systems or devices for providing noise control functionality, including systems or devices for noise detection, noise processing, noise output, feedback, equalization, filtering, adaptive techniques, and/or any other suitable functions. For example, noise control system 20 may include a sound detection system 30, a noise processing system 32, a sound output system 34, a monitoring system 35, and/or one or more other systems or devices.

In some embodiments, noise control system 20 may be partially or fully integrated with ventilation system 14, patient interface 16, and/or connection system 18. Components of sound detection system 30, noise processing system 32, sound output system 34, and/or monitoring system 35 may be partially or fully integrated with ventilation system 14, patient interface 16, and/or connection system 18. In other embodiments, noise control system 20 may be separate or independent from ventilation system 14, patient interface 16, and connection system 18.

Sound detection system 30 may generally be operable to detect noise associated with system 10, e.g., noise caused by gas delivery system 24 and/or one or more components 26. For example, sound detection system 30 may detect noise caused by a motorized blower, noise caused by gasses flowing though system 10 and/or through gas or fluid inlets and/or outlets of system 10, and/or noise associated with the vibration and/or other physical movement of any component of system 10.

Sound detection system 30 may include one or more sensors 36 for direct or indirect sound detection. Sensors 36 for direct sound detection may include, for example, one or more microphones. Sensors 36 for indirect sound detection may include, for example, systems or devices for detecting speed, vibration, or other movement of particular components of system 10, which information may be used to determining one or more characteristics of noise caused by system 10. For example, such sensors 36 may include accelerometers or tachometers.

In some embodiments (e.g., where feed forward noise cancellation is provided), sensors 36 of sound detection system 30 may include (a) one or more reference sensors for detecting noise generated by gas delivery system 24 and/or other components 26, and (b) one or more feedback sensors for providing feedback to determine the effectiveness of noise control system 20.

In other embodiments (e.g., where synchronous feedback noise cancellation is provided), sound detection system 30 may include (a) one or more tachometers, accelerometers, or other suitable devices for detecting the speed, vibration, or other movement of one or more moving components of system 10, which information may be used for determining the tone, pitch, loudness (or amplitude or intensity), quality, and/ or phase, or other characteristic of noise to be controlled, and (b) one or more feedback sensors for providing feedback to determine the effectiveness of noise control system 20.

Sensors 36 may be placed at any suitable location or locations and in any suitable orientation for sensing noise caused by one or more components of system 10. For example, one or more sensors 36 may be located in or proximate gas delivery system 24, patient interface 16, and/or connection system 18. Sensors 36 may be placed at any suitable distance and/or location relative to a noise source to be controlled and/or a noise control speaker 40 used to output noise control signals. For example, one or more sensors 36 may be placed at or near gas delivery system 24 (e.g., a motorized blower), a gas intake port, a gas outlet port, patient interface 16, connection system 18, and/or a noise control speaker 40.

In some embodiments, system 10 may include one or more sensors 36 (e.g., reference sensors) located proximate a noise source to be controlled and one or more sensors 36 (e.g., error, or feedback, sensors) located further away from the noise source or proximate a noise control speaker. For example, as shown in FIG. 1, system 10 may include a reference sensor 36 located in or proximate ventilation system 14 for detecting noise caused by ventilation system 14, one or more noise control speakers 40, and a feedback sensor 36 located away from ventilation system 14 for detecting the perceived noise resulting form the noise source and the output of the noise control speakers, which may be used as feedback for controlling the perceived noise. In some embodiments, the noise control speakers 40 and/or the feedback sensor 36 may be located at or on patient interface 16 or connection system 18. In other embodiments, one or more noise control speakers 40 and/or feedback sensors 36 may be located at or proximate ventilation system 14.

Noise processing system 32 may generally be operable to process noise detected by sound detection system 30 to generate noise control signals operable to control the noise output by system 10. As discussed above, such noise control signals may include, e.g., (a) "noise cancellation signals" for at least partially reducing or canceling the noise output by system 10, (b) "noise leveling signals" for leveling or smoothing the noise output by system 10, both (a) and (b), or any other type and/or combination of signals. Such noise control signals may then be output by sound output system 34, including one or more noise control speakers 40, as discussed below.

Noise control system 20 may use any known or suitable feedback (e.g., synchronous feedback) or feedforward (e.g., adaptive or dynamic equalization) noise control techniques. Thus, noise processing system 32 may include any systems or devices suitable for processing input signals to generate noise control signals for providing such noise control techniques, including one or more feedforward filters, feedback filters, fixed filters, programmable filters, programmable filter controllers, algorithms, amplifiers, speed-noise translators, and/ or any other suitable component(s) arranged in any suitable manner.

Sound output system 34 may generally be operable to output sound signals generated by noise processing system 32, which may include noise control signals (e.g., noise cancellation signals, noise leveling signals, and/or other noise control signals) and/or any other sound signals (e.g., user feedback and/or alarms), such as discussed above. Sound output system 34 may include a noise control speaker 40 and an audio driver 42 operable to control speaker 40. Speaker 40 may be any suitable type of speaker, such as a cone or ribbon-based loudspeaker, for example. In some embodiments, speaker 40 may perform local equalization functions, which may be separate from other equalization or noise control provided by noise control system 20. Audio driver 42 may be any program or device that controls the operation of speaker 40. Audio driver 42 may receive sound signals from noise processing system 32 and translate the received signals in order to control speaker 40 to output sound waves. It should be understood that sound output system 34 may include any suitable number of speakers 40 and/or audio drivers 42.

In some embodiments, sound output system 34 may simultaneously broadcast multiple sound signals. For example, during the operation of system 10, sound output system 34 may simultaneously broadcast multiple types of noise control signals. For instance, sound output system 34 may simultaneously broadcast (a) noise cancellation signals and (b) noise leveling signals, in order to simultaneously reduce and level/ smooth the noise output by system 10. As another example, sound output system 34 may simultaneously broadcast (a) one or more types of noise control signals and (b) one or more other sound signals, e.g., user feedback and/or alarms.

In any of such examples, the multiple different sound signals may be simultaneously broadcast by different speakers 40, or by the same speaker 40. For example, alarm sound signals and noise control signals may be simultaneously delivered to and broadcast by a particular speaker 40. Thus, system 10 may continue to provide noise control functionality during the broadcasting of alarm sound signals.

Example Noise Control System #1

Figure 2:
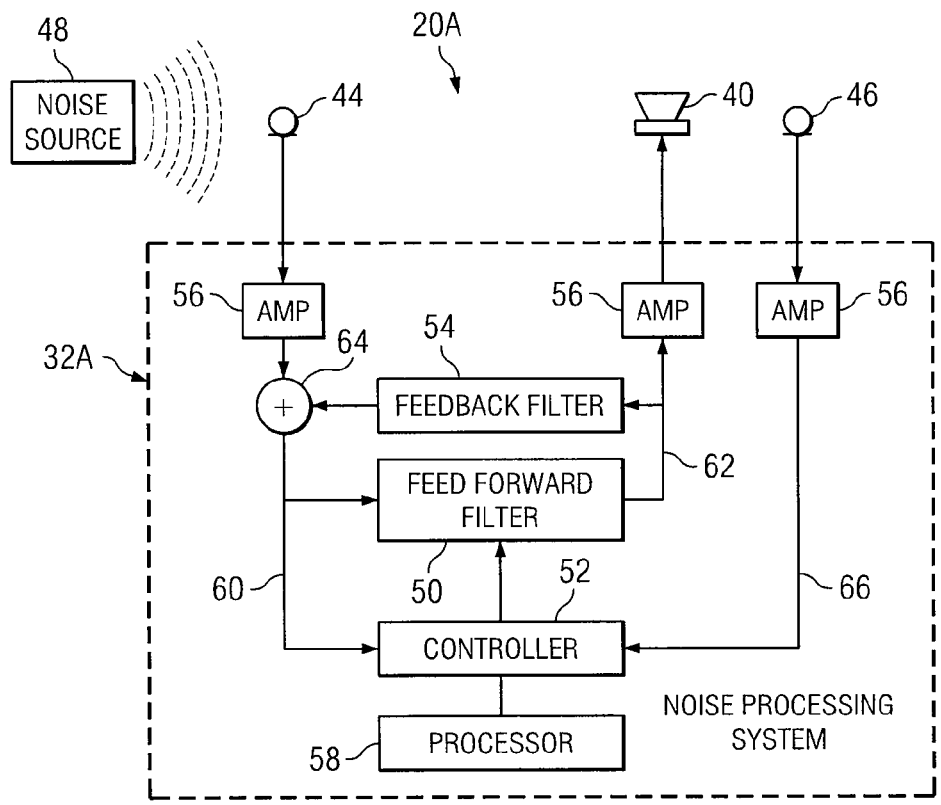
FIG. 2 illustrates an example noise control system for controlling noise caused by a breathing assistance system, in accordance with one embodiment.

As discussed above, in some embodiments, noise control system 20 may use known or suitable noise control techniques. FIG. 2 illustrates an example noise control system 20A for controlling noise caused by breathing assistance system 10, in accordance with one embodiment. Generally, noise control system 20A may detect noise caused by a component of system 10, process the detected noise, and generate noise control signals to control the noise. In this embodiment, noise control system 20A may include one or more reference sensors 44 (e.g., microphones), one or more noise control speakers 40, one or more feedback sensors 46 (e.g., microphones), and a feedforward noise processing system 32A.

Reference sensor(s) 44 may be operable to detect noise generated by a noise source 48 (e.g., gas deliver system 24 or other component 26) and communicate noise signals to noise processing system 32A for processing. Noise control speaker(s) 40 may be operable to receive noise control signals from noise processing system 32A and output such signals to control the noise caused by noise source 48. Feedback sensor(s) 46 may be operable to detect the controlled noise (i.e., the sum of noise caused by noise source 48 and speaker(s) 40) and communicate noise signals as feedback to feedforward noise processing system 32A, such that noise processing system 32A may dynamically adjust noise control signals generated by system 32A.

As shown in FIG. 2, reference sensor(s) 44 may be located relatively close to noise source 48, noise control speaker(s) 40 may be located downstream (i.e., further from noise source 48) from reference sensor(s) 44, and feedback sensor(s) 46 may be located downstream from speaker(s) 40. In some embodiments, reference sensor(s) 44, speaker(s) 40, and feedback sensor(s) 46 may be located inside or proximate a duct or conduit leading from noise source 48. For example, reference sensor(s) 44, speaker(s) 40, and feedback sensor(s) 46 may be located inside or proximate a gas conducting conduit (e.g., a gas inlet or gas outlet conduit) of system 10. In addition, one, some, or all of reference sensor(s) 44, speaker(s) 40, and feedback sensor(s) 46 may be located either inside or outside of any internal or external casing or housing of system 10.

Noise processing system 32A may include any systems, devices, or logic for providing one or more types of feedforward noise control, e.g., adaptive or dynamic equalization. For example, system 32A may provide (a) noise cancellation, (b) noise leveling, (c) both noise cancellation and noise leveling, or (d) one or more other types of noise control. In the example embodiment shown in FIG. 2, noise processing system 32A may provide both noise cancellation and noise leveling. System 32A may include a feedforward filter 50, a feedforward filter controller 52, a feedback filter 54, one or more amplifiers 56, one or more processors 58, and/or any other suitable component(s). As used herein, the term "feedforward filter" may refer to an equalizer (e.g., an adaptive, dynamic, or feedback equalizer) or any other known or suitable feedforward filter.

Feedforward filter 50 may be a controllable or programmable filter that may be dynamically controlled by feedforward filter controller 52 to provide one or more types of noise control, e.g., (a) noise cancellation, (b) noise leveling, (c) both noise cancellation and noise leveling, or (d) one or more other types of noise control. As shown in FIG. 2, feedforward filter 50 may filter or process input signals 60 to generate noise control signals 62 to be output by speaker 40. Input signals 60 may include signals received from reference sensor 44 and signals received from feedback filter 54, which may be mixed as indicated at 64. Feedforward filter 50 may be any suitable type of filter, such as a finite impulse response (FIR) filter or an infinite impulse response (IIR) filter, for example.

Feedforward filter controller 52 may be operable to dynamically control feedforward filter 50 (e.g., by adjusting one or more variables or parameters of feedforward filter 50) based on input signals 60 and feedback, or error, signals 66 received from feedback sensor 46. Feedforward filter controller 52 may control feedforward filter 50 to provide one or more types of noise control, as discussed above. Feedforward filter controller 52 may include or have access to processor 58 and any suitable algorithms or other executable code that may be executed by processor 58 for dynamically controlling feedforward filter 50 to generate noise control signals. For example, controller 52 may include a "least mean square" (LMS) algorithm.

Feedback filter 54 may be operable to filter noise control signals 62 generated by feedforward filter 50 to provide as feedback in order to compensate for the fact that noise control signals output by speaker 40 are picked up by reference sensor 44. Feedback filter 54 may be any suitable type of filter, such as a finite impulse response (FIR) filter or an infinite impulse response (IIR) filter, for example. In some embodiments, feedback filter 54 may be a fixed filter (as opposed to programmable or controllable feedforward filter 50).

Amplifiers 56 may be used to amplify any signals associated with noise control system 20, e.g., noise signals detected or communicated by sensors 36 and/or noise control signals generated by noise processing system 32A.

Processor 58 may be operable to access and execute any suitable algorithms or logic associated with feedforward noise control system 20A. Such algorithms or logic may be stored in any suitable data storage medium. Processor 58 may comprise any type of processor, such as a digital signal processor (DSP), a microcontroller, or a field-programmable gate array (FPGA), for example. In embodiments in which processor 58 comprises an FPGA, the functionality of various algorithms or logic may instead be programmed into the FPGA rather than provided as separate code.

In some embodiments, processor 58 may provide one or more operations not directly related to feedforward noise control system 20A. For example, processor 58 may control the operation (e.g., the motor speed and on/off control) of a motorized blower supplying pressurized gas to patient 12. As another example, processor 58 may generate other sound signals (i.e., signals other than noise control signals 62) to be broadcast by sound output system 34, such as user feedback (e.g., instructions or other words), or other sounds regarding the operation of system 10. For example, processor 58 may monitor the operation of system 10 and, when appropriate, generate alarm signals (e.g., a siren, buzzer, or words) to be broadcast by sound output system 34. Thus, processor 58 may provide one, all, or any combination of the following functions: (a) controlling the operation of gas delivery system 24, (b) monitoring the operation of system 10 and/or generating alarm signals to be broadcast by sound output system 34, (c) detecting correct/incorrect operation of one or more components of system 10, (d) generating user feedback signals to be broadcast by sound output system 34, and/or (e) generating noise control signals 62 to be broadcast by sound output system 34 for controlling noise caused by system 10. In other embodiments, noise control system 20A has one or more dedicated processors 58, and one or more other processors are provided for performing other functions of system 10 such as listed above.

Example Noise Control System #2

Figure 3:
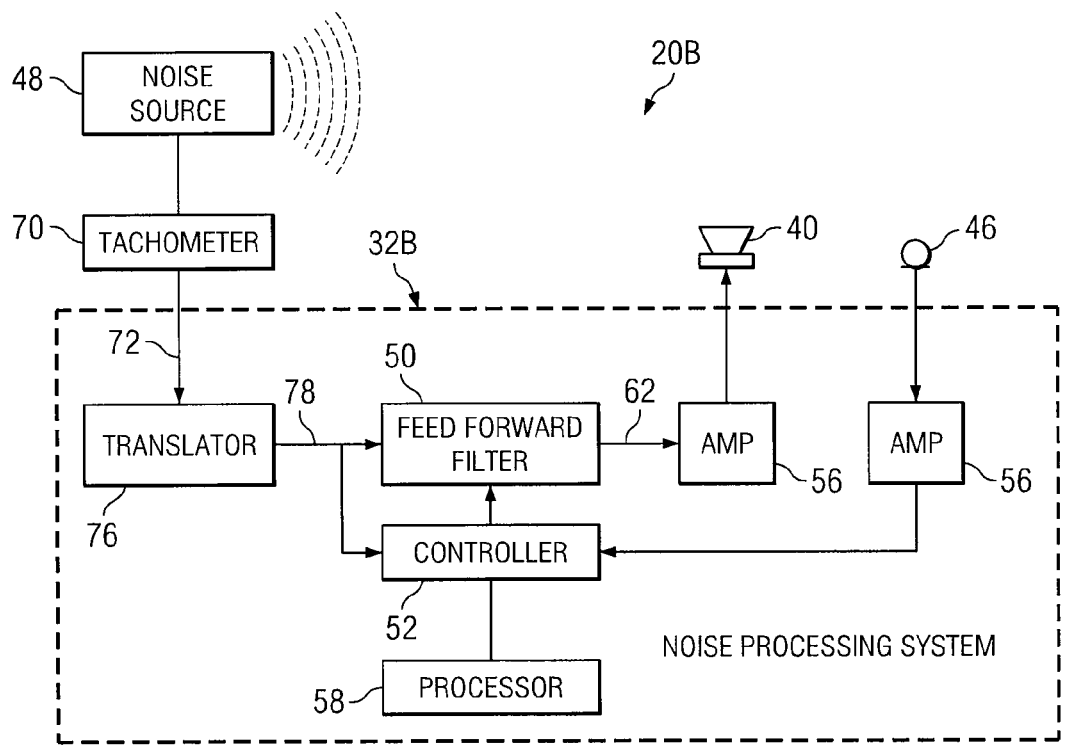
FIG. 3 illustrates another example noise control system for controlling noise caused by a breathing assistance system, in accordance with another embodiment.

FIG. 3 illustrates an example noise control system 20B for controlling noise caused by breathing assistance system 10, in accordance with another embodiment. Generally, noise control system 20B may detect the speed of a moving component of system 10 (e.g., a motorized blower), determine the noise corresponding with such speed, and generate noise control signals to control the determined noise. In this embodiment, noise control system 20B may include a tachometer 70, one or more noise control speakers 40, one or more feedback sensors 46 (e.g., microphones), and a noise processing system 32B.

Tachometer 70 may be operable to detect the speed of a moving component of a noise source 48 (e.g., the rotational speed of a motor or shaft associated with a blower fan), and communicate tachometer signals 72 to noise processing system 32B for processing. Noise control speaker(s) 40 may be operable to receive noise control signals 62 from noise processing system 32B and output such signals to control the noise caused by noise source 48. Feedback sensor(s) 46 may be operable to detect the controlled noise (i.e., the sum of noise caused by noise source 48 and speaker(s) 40) and communicate noise signals as feedback to noise processing system 32B, such that noise processing system 32B may dynamically adjust noise control signals 62 generated by system 32B.

Speaker(s) 40 and feedback sensor(s) 46 may be located at any suitable location relative to each other and relative to other components of system 10. Speaker(s) 40 and/or feedback sensor(s) 46 may be located either inside or outside of any internal or external casing or housing of system 10.

Noise processing system 32B may include any systems, devices, or logic for providing one or more types of feedback noise control. For example, system 32B may provide (a) noise cancellation, (b) noise leveling, (c) both noise cancellation and noise leveling, or (d) one or more other types of noise control. In the example embodiment shown in FIG. 3, noise processing system 32B may provide both noise cancellation and noise leveling. System 32B may include a speed-noise translator 76, a feedforward filter controller 52, one or more amplifiers 56, one or more processors 58, and/or any other suitable component(s).

Speed-noise translator 76 may be operable to process tachometer signals 72 to generate input signals 78 that may be used by feedforward filter 50 for generating noise control signals 62 to control the noise caused by noise source 48. For example, speed-noise translator 76 may comprise a harmonic generator operable to process tachometer signals 72 to provide pure (or substantially pure) tones at the harmonics of noise source 48. Thus, noise processing system 32B may focus on the noise caused by noise source 48.

Feedforward filter 50 may be a controllable or programmable filter that may be dynamically controlled by feedforward filter controller 52 to provide one or more types of noise control, e.g., (a) noise cancellation, (b) noise leveling, (c) both noise cancellation and noise leveling, or (d) one or more other types of noise control. As shown in FIG. 3, feedforward filter 50 may filter or process input signals 78 received from speed-noise translator 76 to generate noise control signals 62 to be output by speaker 40. Feedforward filter 50 may be any suitable type of filter, such as a finite impulse response (FIR) filter or an infinite impulse response (IIR) filter, for example.

Feedforward filter controller 52 may be operable to dynamically control feedforward filter 50 (e.g., by adjusting one or more variables or parameters of feedforward filter 50) based on input signals 60 and error signals 66 received from feedback sensor 46. Feedforward filter controller 52 may control feedforward filter 50 to provide one or more types of noise control, as discussed above. Feedforward filter controller 52 may include or have access to processor 58 and any suitable algorithms or other executable code that may be executed by processor 58 for dynamically controlling feedforward filter 50 to generate noise control signals. For example, controller 52 may include a "least mean square" (LMS) algorithm.

Amplifiers 56 may be used to amplify any signals associated with noise control system 20, e.g., noise signals detected or communicated by sensors 36 and/or noise control signals generated by noise processing system 32B.

Processor 58 may be operable to access and execute any suitable algorithms or logic associated with noise control system 20B. Such algorithms or logic may be stored in any suitable data storage medium. Processor 58 may comprise any type of processor, such as a digital signal processor (DSP), a microcontroller, or a field-programmable gate array (FPGA), for example. In embodiments in which processor 58 comprises an FPGA, the functionality of various algorithms or logic may instead be programmed into the FPGA rather than provided as separate code.

In addition, as discussed above, in some embodiments regarding feedforward noise control system 20A, processor 58 may provide one or more operations not directly related to noise control system 20B.

Example Noise Control System #3

Figure 4:
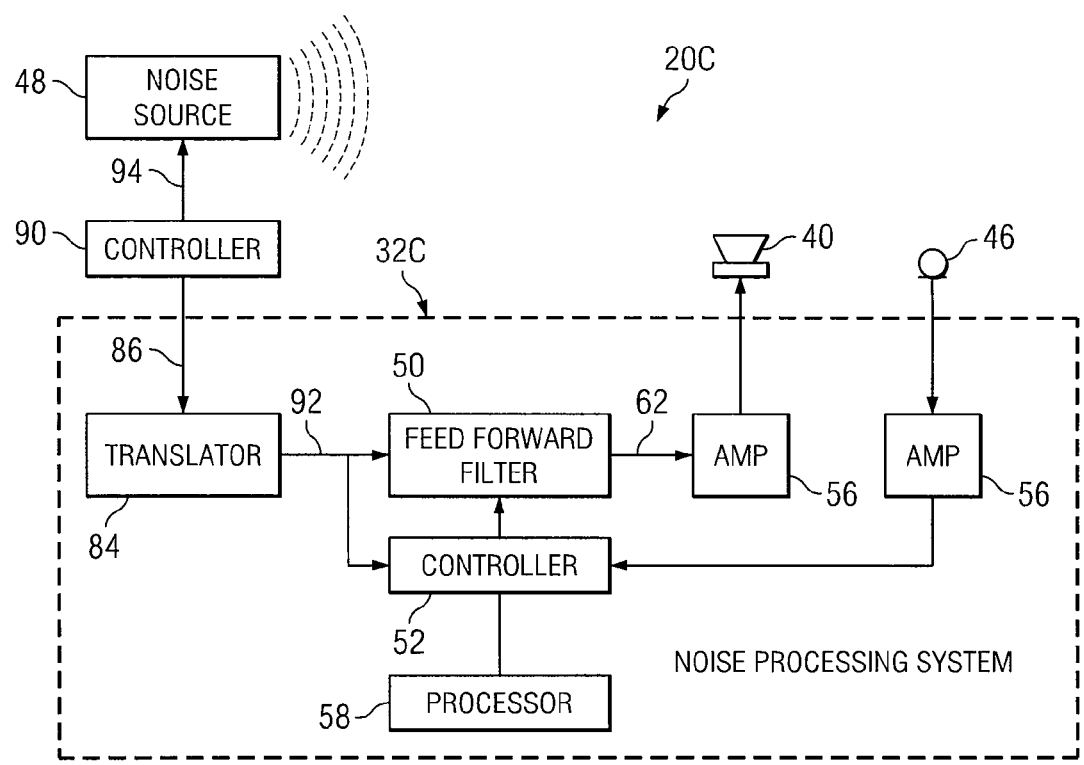
FIG. 4 illustrates yet another example noise control system for controlling noise caused by a breathing assistance system, in accordance with another embodiment.

FIG. 4 illustrates an example noise control system 20C for controlling noise caused by breathing assistance system 10, in accordance with another embodiment. Noise control system 20C may generally be operable to receive control data regarding the speed of a moving component of system 10 (e.g., a motorized blower), determine the noise corresponding with such speed, and generate noise control signals to control the determined noise. As opposed to Example System #2 discussed above, in which the actual speed of the moving component is detected and used for generating noise control signals, in Example System #3 signals used to control the speed of the moving component are used for generating noise control signals. Thus, the actual speed of the component need not be actually measured.

In this embodiment, noise control system 20C may include one or more noise control speakers 40, one or more feedback sensors 46 (e.g., microphones), and a noise processing system 32C.

Noise control speaker(s) 40 may be operable to receive noise control signals 62 from noise processing system 32C and output such signals to control the noise caused by noise source 48. Feedback sensor(s) 46 may be operable to detect the controlled noise (i.e., the sum of noise caused by noise source 48 and speaker(s) 40) and communicate noise signals as feedback to noise processing system 32C, such that noise processing system 32C may dynamically adjust noise control signals 62 generated by system 32C.

Speaker(s) 40 and feedback sensor(s) 46 may be located at any suitable location relative to each other and relative to other components of system 10. Speaker(s) 40 and/or feedback sensor(s) 46 may be located either inside or outside of any internal or external casing or housing of system 10.

Noise processing system 32C may include any systems, devices, or logic for providing one or more types of feedback noise control. For example, system 32B may provide (a) noise cancellation, (b) noise leveling, (c) both noise cancellation and noise leveling, or (d) one or more other types of noise control. In the example embodiment shown in FIG. 3, noise processing system 32C may provide both noise cancellation and noise leveling. System 32C may include a speed-noise translator 90, a feedforward filter controller 52, one or more amplifiers 56, one or more processors 58, and/or any other suitable component(s).

Speed-noise translator 84 may be operable to process control signals 86 from a controller 90 to generate input signals 92 that may be used by feedforward filter 50 and/or feedforward filter controller 52 for generating noise control signals 62. Controller 90 may generate control signals 94 for controlling the operation of a moving component of noise source 48. For example, controller 90 may generate control signals 94 for controlling the speed and/or acceleration of a motorized blower. Speed-noise translator 84 may access any suitable algorithms or look-up tables for processing control signals 86 to generate appropriate input signals 92.

As discussed above, feedforward filter 50 may be a controllable or programmable filter that may be dynamically controlled by feedforward filter controller 52 to provide one or more types of noise control, e.g., (a) noise cancellation, (b) noise leveling, (c) both noise cancellation and noise leveling, or (d) one or more other types of noise control.

As discussed above, feedforward filter controller 52 may be operable to dynamically control feedforward filter 50 (e.g., by adjusting one or more variables or parameters of feedforward filter 50) based on input signals 96 and error signals 66 received from feedback sensor 46. Feedforward filter controller 52 may control feedforward filter 50 to provide one or more types of noise control, as discussed above. Feedforward filter controller 52 may include or have access to processor 58 and any suitable algorithms or other executable code that may be executed by processor 58 for dynamically controlling feedforward filter 50 to generate noise control signals. For example, controller 52 may include a "least mean square" (LMS) algorithm. Amplifiers 56 and processor 58 may be similar to those described above.

Noise Reduction/Cancellation

In some embodiments (e.g., using any of the example noise control systems discussed above), noise control signals produced by noise control system 20 (e.g., system 20A and/or 20B) may include noise cancellation signals operable to reduce or cancel noise caused by a noise source 48. The noise cancellation signals may be designed to reduce or cancel at least a portion of the noise caused by noise source 48. Noise processing system 32 may generate any type of noise cancellation signals in any suitable manner, e.g., using any known or suitable algorithms and/or techniques. For example, noise processing system 32 may generate noise cancellation signals having the same or directly proportional amplitude and the opposite polarity (i.e., a polarity reversed waveform) as the detected noise waves, which noise cancellation signals may be used to reduce the amplitude of (or otherwise reduce or cancel) the perceived noise. As another example (or in addition to polarity reversing techniques), noise processing system 32 may use phase shifting (e.g., rotating frequencies 180 degrees out of phase) to generate noise cancellation signals. Any other known or suitable techniques may be used to generate the noise cancellation signals.

Figure 5:
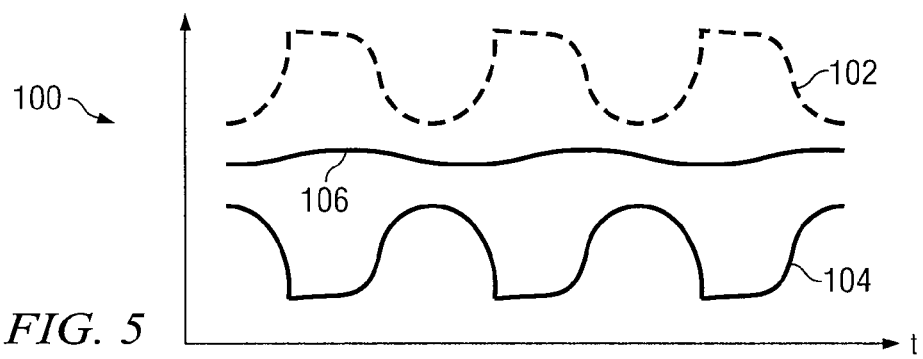
FIG. 5 illustrates an example graph illustrating the effects of noise cancellation signals, according to one embodiment.

FIG. 5 illustrates an example graph 100 illustrating the effects of noise cancellation signals, according to one embodiment. Graph 100 illustrates (a) noise caused by noise source 48 (indicated at 102), and (b) noise cancellation signals generated by noise processing system 32 (indicated at 104), and (c) the resulting perceived noise from noise source 48 and noise cancellation signals (indicated at 106), each as a function of time. The units for the y-axis in graph 100 may be any measurement of noise magnitude, such as dBA, for example. The extent of noise reduction or cancellation may vary as a function of one or more parameters (e.g., tone, pitch, loudness (or amplitude or intensity), quality, and/or phase) of the noise caused by system 10, or may otherwise vary over time.

Noise Leveling/Smoothing

In some embodiments (e.g., using any of the example noise control systems discussed above), noise control signals produced by noise control system 20 (e.g., system 20A and/or 20B) may include noise leveling signals for leveling or smoothing the noise caused by a noise source 48. The noise leveling signals may be designed to be added to the noise caused by noise source 48 to maintain (or attempt to maintain) the perceived noise from noise source 48 constant over time. Thus, in contrast to noise cancellation signals which are designed to cancel target noises, noise leveling signals may be generally designed to be added to target noises in order to maintain the total perceived noise (i.e., the target noise plus the noise leveling signals) relatively constant over time.

For example, the noise leveling signals may reduce variations in one or more sound characteristics (e.g., tone, pitch, loudness (or amplitude or intensity), quality, and/or phase) of the perceived noise from noise source 48 over time. For instance, where noise source 48 comprises a variable-speed blower motor, noise leveling signals may be designed to maintain the perceived tone, pitch and/or loudness of variable noise caused by the variable-speed blower motor relatively constant over time.

In order to level the perceived noise from noise source 48, the noise leveling signals may exhibit one, some, or all of the following characteristics:

one or more sound characteristics of noise leveling signals (e.g., tone, pitch, loudness (or amplitude or intensity), quality, and/or phase) may be designed to mimic, or may be directly proportional (linearly, exponentially, or otherwise) to, the noise to be leveled; and/or one or more other sound characteristics of noise leveling signals may be inversely proportional (linearly, exponentially, or otherwise) to the noise to be leveled; and/or one or more other sound characteristics of noise leveling signals may adjust dynamically in order to maintain one or more varying sound characteristics (e.g., tone, pitch, loudness (or amplitude or intensity), quality, and/or phase) of the noise to be leveled relatively constant over time.

For example, the loudness (or amplitude or intensity) of the noise leveling signals may have an inverse relationship (linearly, exponentially, or otherwise) with the loudness of the noise to be leveled. Thus, when the loudness of the noise to be leveled increases (e.g., where a blower motor speed increases), the loudness of the generated noise leveling signals decreases. Similarly, when the loudness of the noise to be leveled decreases (e.g., where a blower motor speed decreases), the loudness of the generated noise leveling signals increases. In this manner, the resulting total noise (i.e., the noise caused by the noise source plus the noise leveling signals) may be maintained relatively constant over time.

As another example, the pitch of the noise leveling signals may be designed to maintain the perceived pitch of the noise to be leveled relatively constant over time. For instance, when the pitch of the noise to be leveled increases or decreases (e.g., where a blower motor speed increases or decreases), the pitch of the generated noise leveling signals may be adjusted such that the pitch of the resulting total noise (i.e., the noise caused by the noise source plus the noise leveling signals) may be maintained relatively constant over time.

Noise processing system 32 may generate any type of noise leveling signals in any suitable manner, e.g., using any known or suitable algorithms and/or techniques. Such algorithms and/or techniques may or may be not be similar or analogous to algorithms and/or techniques used for generating noise cancellation signals as discussed above.

Figure 6:
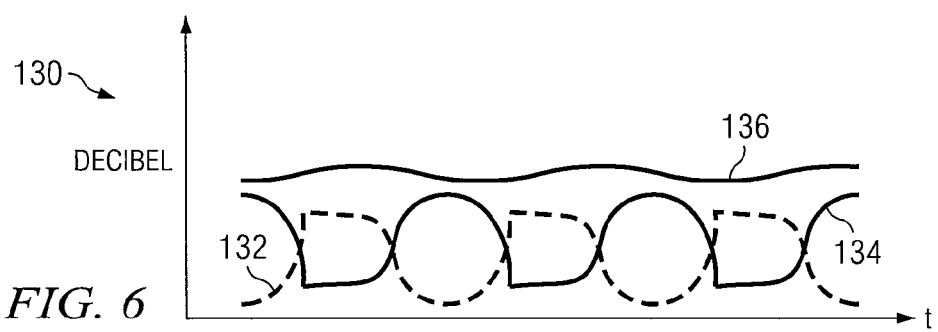
FIG. 6 illustrates an example graph illustrating the effects of noise leveling signals, according to one embodiment.

FIG. 6 illustrates an example graph 130 illustrating the effects of noise leveling signals, according to one embodiment. Graph 130 illustrates (a) noise caused by noise source 48 (indicated at 132), and (b) noise leveling signals generated by noise processing system 32 (indicated at 134), and (c) the resulting perceived noise from noise source 48 and noise cancellation signals (indicated at 136), each as a function of time, according to one embodiment. In this embodiment, the noise leveling signals are designed to be added to the noise caused by noise source 48 in order to provide the relatively constant total sound output 136.

Noise Reduction/Cancellation+Noise Leveling/Smoothing

In some embodiments (e.g., using any of the example noise control systems discussed above), noise control signals produced by noise control system 20 (e.g., system 20A, 20B or 20C) may include both noise cancellation and noise leveling signals (which may be combined) for simultaneously reducing and leveling the perceived noise from noise source 48. Such noise control signals are referred to below as noise cancellation/leveling signals.

Noise processing system 32 may generate noise cancellation/leveling signals using any known or suitable systems or techniques (e.g., any known or suitable components, arrangement of components, feedback loops, and/or algorithms) including, for example, any of the systems or techniques discussed herein for providing noise cancellation or noise leveling functionality.

In some embodiments, noise processing system 32 may perform the noise cancellation and noise leveling functions separately, and may use separate filters, controllers, algorithms, and/or feedback loops for performing the noise cancellation and noise leveling functions. The noise cancellation and noise leveling processing may be performed serially or in parallel. Where the noise cancellation and noise leveling processing are performed serially, the noise cancellation may be performed either before or after the noise leveling, depending on the particular embodiment.

In other embodiments, noise processing system 32 may perform the noise cancellation and noise leveling functions partially or completely simultaneously. In such embodiments, one or more filters and/or filter controllers may use algorithms designed to provide both noise cancellation and noise leveling functions simultaneously.

Example Configurations of Noise Control System 20

Figure 7:
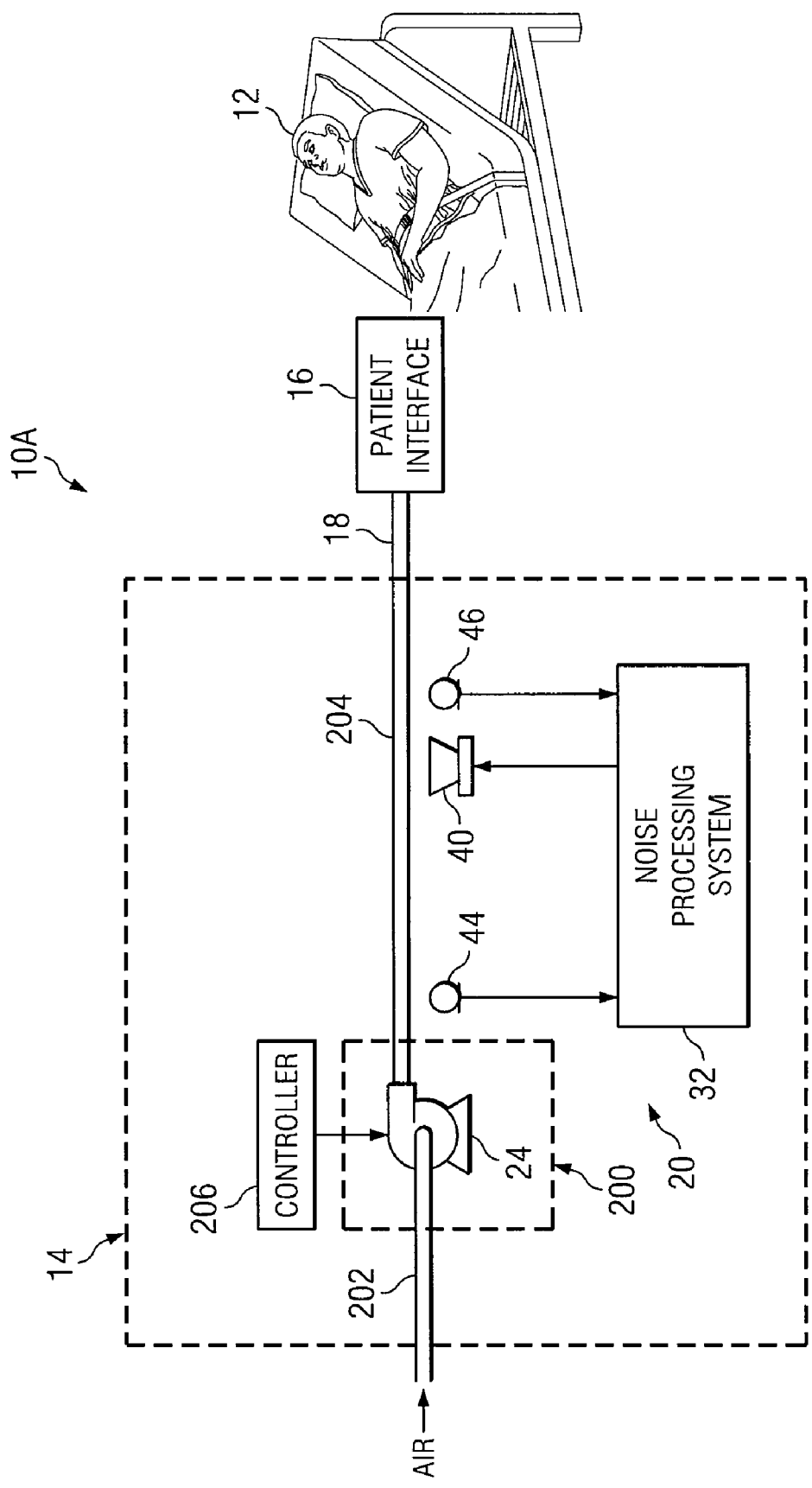
FIG. 7 illustrates an example breathing assistance system having active noise control functionality for controlling noise produced by a blower motor, in accordance with one embodiment.

FIG. 7 illustrates an example breathing assistance system 10 having active noise control functionality in accordance with one embodiment. System 10A may include a ventilation system 14, a patient interface 16, a connection system 18, and a noise control system 20. Ventilation system 14 may include gas delivery system 24, insulation 200 disposed around gas delivery system 24, a gas inlet conduit 202, a gas outlet conduit 204, a controller 206, other ventilation system components 16. Noise control system 20 may be at least partially integrated with ventilation system 14, and may include a noise processing system 32, a noise control speaker 40, a reference sensor 44, a feedback sensor 46, and/or any other suitable components. In some embodiments, system 10A may be a compact, portable system, such as a system for home use. In other embodiments, system 10A may be a larger, more complex system, such as for use in a hospital.

In this example embodiment, gas delivery system 24 comprises a motorized blower 24 controlled by controller 206 based on various input (e.g., data received from one or more sensors and/or user input). Blower 24 may generally be operable to receive atmospheric air via gas inlet conduit 202, pressurize the air, and deliver the pressurized air toward patient 12 through gas outlet conduit 204. In one embodiment, blower 24 may be manufactured by TECHNOFAN S.A., having a location at 10A, Place Marcel-Dassault, Zac du Grand Noble, Blagnac Cedex 31702, France.

Insulation 200 may be disposed partially or substantially completely around gas delivery system 24 and may comprise any suitable materials for providing passive sound reduction, e.g., any suitable types of foam, rubber, fiberglass, wood, latex, polyurethane, or any suitable composite materials.

As discussed above, speaker 40 and sensors 44 and 46 may be placed at any suitable location or locations and in any suitable orientation for sensing noise associated with system 10A. In this example embodiment, reference sensor 44 may be located near blower 24, speaker 40 may be located further from blower 24 (e.g., generally downstream from reference sensor 44 along gas outlet conduit 204 or another conduit or duct), and feedback sensor 46 may be located near speaker 40 (e.g., downstream from speaker 40 along gas outlet conduit 204 or another conduit or duct).

As discussed above (e.g., regarding FIG. 2), reference sensor 44 may detect noise caused by blower 24 and send noise signals to noise processing system 32. Feedback sensor 46 may detect noise caused by blower 24 and speaker 40 and provide noise signals as feedback to noise processing system 32. Noise processing system 32 may generate noise control signals for output by speaker 40 based on the signals received from both reference sensor 44 and feedback sensor 46. Noise processing system 32 may use any suitable algorithms and techniques to generate noise control signals for controlling (e.g., reducing/canceling and/or leveling/smoothing) the noise generated by blower 24.

In this manner, system 10A may include both passive noise control (using insulation 200) and active noise control (using noise processing system 32), which may be desirable to patient 12 and others within audible range of system 10A. In some embodiments, such a combination of passive and active noise control may be used to provide a desirable set of parameters, such as the type or level of noise control and/or the weight and/or size of the system.

Figure 8:
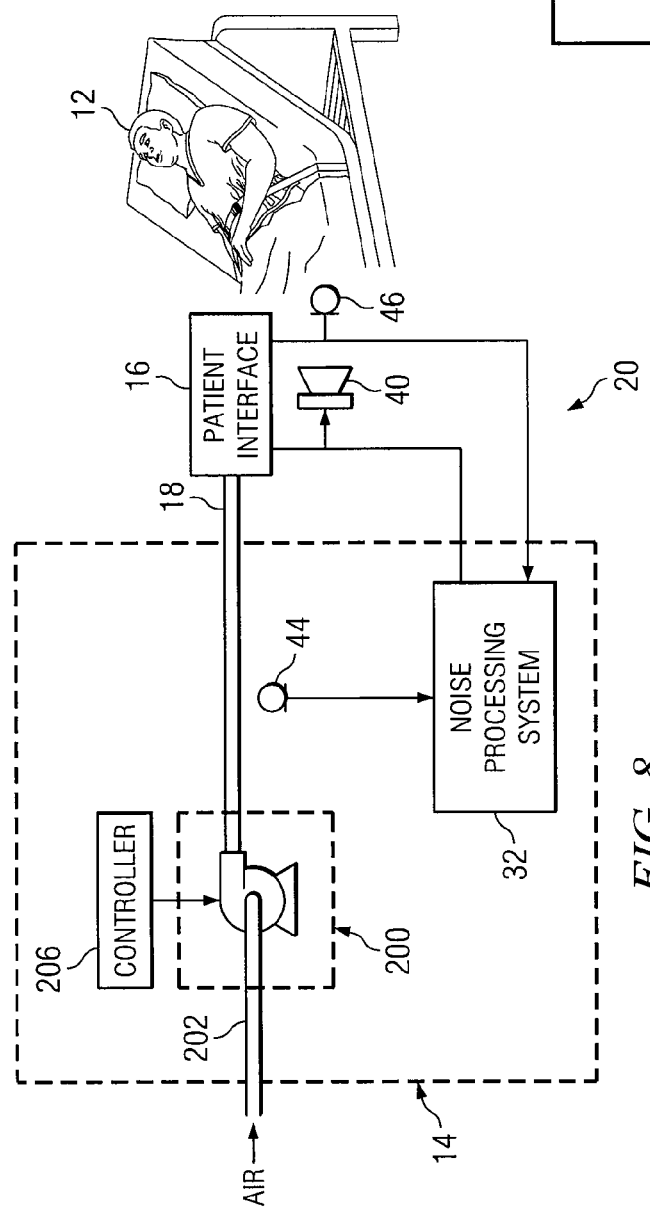
FIG. 8 illustrates another example breathing assistance system having active noise control functionality for controlling noise produced by a blower motor, in accordance with one embodiment.

FIG. 8 illustrates another example breathing assistance system 10B having active noise control functionality in accordance with one embodiment. System 10B may include a ventilation system 14, a patient interface 16, a connection system 18, and a noise control system 20. System 10B may be similar to system 10A shown in FIG. 7, except particular components of noise control system 20 in system 10B may be located closer to patient 12. For example, as shown in FIG. 8, speaker 40 and/or feedback sensor 46 may be located at, or integrated into, patient interface 16 and/or connection system 18. In other embodiments, speaker 40 and/or feedback sensor 46 may be otherwise located near patient 12, e.g., coupled to the patient's bed or a wall proximate patient 12. Speaker 40 and/or feedback sensor 46 may be coupled to ventilation system 10 and/or noise processing system 32 in any suitable manner, e.g., via wires running along connection system 18 or via wireless links.

Monitoring/Fault Detection

Figure 9:
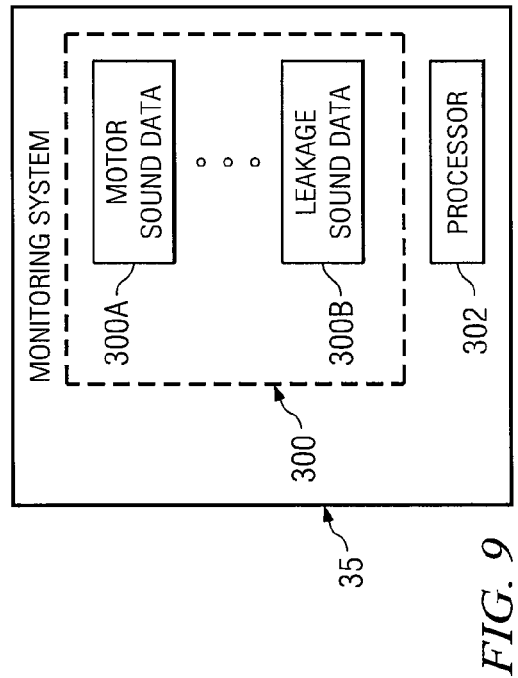
FIG. 9 illustrates an example monitoring system 35 for monitoring system 10 based at least on detected sound signals, according to one embodiment of the disclosure.

FIG. 9 illustrates an example monitoring system 35 for monitoring system 10 based at least on detected sound signals, according to one embodiment of the disclosure. Monitoring system 35 may be generally operable to monitor one or more components or functions of system 10 based on detected sound signals, e.g., to detect faults and/or determine whether particular components or functions of system 10 are working properly. For example, in some embodiments, monitoring system 35 may be configured to analyze the operation of a motor or other sound-producing component of gas delivery system 24 and/or to detect gas leakage at one or more locations of system 10.

As shown in FIG. 9, monitoring system may include one or more sets of sound data 300 and a processor 302. Sound data 300 may include any stored data (e.g., sound spectral patterns) regarding sounds produced by or associated with components and/or functions of system 10. For example, sound data 300 may include motor sound data 300A, leakage sound data 300B, and/or any other type of sound data.

Motor sound data 300A may include any sound data associated with a motor of system 10 (e.g., a blower motor), such as sounds associated with the motor (or a motor of the same type) operating properly, or during the early stages of the motor's lifespan, and/or sounds associated with motor failures, an aging motor, or other qualities of the motor. In some embodiments, motor sound data 300A may be pre-recorded (e.g., from testing and recording of similar motors operating under various conditions, at various stages of the motor lifespan, while experiencing various types of faults, etc.) and loaded into monitoring system 35. In other embodiments, motor sound data 300A may be recorded during the operation of system 10, stored, and used for analyzing the motor sounds over time. For example, sounds produced by the motor during the early stages of the motor's life may be stored and compared with sounds produced by the motor as the motor ages, in order to analyze the condition of the motor as the motor ages and/or to detect motor faults.

Leakage sound data 300B may include any sound data associated with gas leaks at one or more locations of system 10, e.g., between connected components of system 10, such as between connection system 18 and ventilation system 14, between connection system 18 and patient interface 16, and/or between patient interface 16 and the patient's face. In some embodiments, leakage sound data 300B may be pre-recorded (e.g., from testing and recording sounds of leaks at one or more locations of system 10 or a similar system), and loaded into monitoring system 35. In other embodiments, leakage sound data 300B may be recorded during the operation of system 10, stored, and used for analyzing the leakage sounds over time. For example, sounds detected near a potential leak area may be recorded and compared over time to determine changes in the sounds that may indicate a leak.

Processor 302 may be configured to receive raw or processed sound data from sound detection system 30 and/or noise processing system 32, and analyze such sounds to monitor one or more components or functions of system 10, e.g., to detect faults, to detect leaks, and/or to determine the operational condition of particular components of system 10. For example, processor 302 may analyze motor sound data, which may include comparing received sound data regarding a motor (e.g., from one or more microphones or other sensors located near the motor) with stored motor sound data 300A to monitor the status of the motor. Processor 302 may access any suitable algorithms, software, or other logic to perform such analysis. In this manner, processor 302 may determine, e.g., whether the motor is operating properly, operating improperly, experiencing a fault, or needs to be replaced.

As another example, processor 302 may analyze leakage sound data, which may include comparing received leakage sound data (e.g., from one or more microphones or other sensors located near source of potential leaks), which may or may not be audible to a human, with stored leakage sound data 300B to monitor the presence and/or magnitude of gas leaks. Again, processor 302 may access any suitable algorithms, software, or other logic to perform such analysis.

Processor 302 may communicate the results of any analysis in any suitable manner. For example, processor 302 may communicate data (e.g., alerts, alarms, or status information) for display on a display associated with system 14, may communicate sound signals (e.g., alerts, alarms, or status information) for output by sound output system 34, or may otherwise communicate data to a user of system 10.

Although the disclosed embodiments have been described in detail, it should be understood that various changes, substitutions and alterations can be made to the embodiments without departing from their spirit and scope.

What is claimed is:

1. A breathing assistance system having active noise control, the system comprising:
    a gas delivery system operable to supply breathing gas;
    a patient interface configured to interface with a patient for delivering breathing gas to one or more breathing passages of the patient;
    a connection system configured to communicate breathing gas supplied by the gas delivery system to the patient interface for delivery to the patient; and
    a noise control system configured to control noise caused by a noise source associated with the breathing assistance system, the noise control system including:
        a processor configured to generate noise control signals for at least partially canceling noise caused by the noise source;
        controller configured to:
            generate noise source control signals for controlling the operation of the noise source; and
            communicate the noise source control signals to the processor;
        a speaker operable to output the noise control signals generated by the processor for at least partially canceling noise caused by the noise source; and
        a feedback sensor configured to detect noise caused by the noise source and noise control signals output by the speaker, and communicate to the processor feedback noise signals based on the detected noise;
        wherein the processor is configured to generate the noise control signals based at least on the noise source control signals from the controller and the feedback noise signals from the feedback sensor.

2. A breathing assistance system according to claim 1, wherein at least one of the speaker and the feedback sensor is located away from the gas delivery system and proximate the patient.

3. A breathing assistance system according to claim 1, wherein at least one of the speaker and the feedback sensor is located at the patient interface or the connection system.

4. A breathing assistance system according to claim 1, wherein:
    the controller is located a first distance from the noise source; and
    the speaker and the feedback sensor are located further than the first distance from noise source.

5. A breathing assistance system according to claim 1, wherein the noise source comprises the gas delivery system.

6. A breathing assistance system according to claim 1, wherein:
    the noise source has an associated speed; and
    the noise source control signals identify the speed of the noise source set by the controller.

7. A breathing assistance system according to claim 6, wherein the controller is configured to control the speed of the noise source.

8. A breathing assistance system according to claim 1, wherein the noise control system further includes a translator configured to receive reference signals from the controller, translate the reference signals, and communicate the translated reference signals toward the processor.

9. A breathing assistance system according to claim 1, wherein the gas delivery system comprises a motorized blower.

10. A breathing assistance system according to claim 1, wherein the noise control system is configured to control noise caused by gas flowing through one or more passageways associated with the breathing assistance system.

11. A breathing assistance system according to claim 1, wherein the speaker is operable to output audible feedback regarding the operation of the breathing assistance system in addition to outputting the noise control signals.

12. A breathing assistance system according to claim 1, wherein the noise control signals provide both noise cancellation and noise leveling functions, wherein noise leveling comprises leveling the perceived noise over a plurality of breath cycles.

13. A noise control system for controlling noise associated with a breathing assistance system, the noise control system comprising:
    a processor configured to generate noise control signals for at least partially canceling noise associated with a noise source of a breathing assistance system;

a controller configured to:
  generate noise source control signals for controlling the operation of the noise source; and
  communicate the noise source control signals to the processor;
a speaker operable to output the noise control signals generated by the processor for at least partially canceling noise caused by the noise source; and
a feedback sensor configured to:
  detect noise caused by the noise source and noise control signals output by the speaker; and
  communicate to the processor feedback noise signals based on the detected noise;
wherein the processor is configured to generate the noise control signals based at least on the noise source control signals from the controller and the feedback noise signals from the feedback sensor.

14. A noise control system according to claim 13, wherein:
the breathing assistance system includes a ventilation system; and
at least one of the speaker and the feedback sensor is located away from the ventilation system and proximate the patient.

15. A noise control system according to claim 13, wherein:
the breathing assistance system includes a device having an associated speed; and
the noise source control signals identify the speed of the device set by the controller.

16. A noise control system according to claim 15, wherein the device comprises a motorized blower.

17. A noise control system according to claim 13, further comprising a translator configured to receive reference signals from the controller, translate the reference signals, and communicate the translated reference signals toward the processor.

18. A system for providing active noise control in a breathing assistance system, the system comprising:
a gas delivery device operable to supply pressurized gas for a breathing assistance system;
a controller operable to generate gas delivery device control signals for controlling the operation of the gas delivery device;
a processor operable to receive the gas delivery device control signals from the controller, and generate noise cancellation signals based at least on the gas delivery device control signals, the noise cancellation signals operable to at least partially cancel the noise associated with the breathing assistance system; and
a speaker operable to output the generated noise control signals for at least partially reducing the noise caused associated with the breathing assistance system.

19. A method for controlling noise associated with a breathing assistance system, the method comprising:
using a controller to control the operation of a noise source of a breathing assistance system;
communicating the noise source control signals as reference signals to a processor;
using a speaker to output noise control signals for at least partially canceling the noise caused by the noise source;
using a second sensor to detect (a) noise caused by the noise source and (b) noise control signals output by the speaker;
communicating to the processor feedback signals based on the noise detected by the second sensor; and
using the processor to generate noise control signals for output by the speaker based at least on the received reference signals and feedback signals.

20. A method according to claim 19, wherein the noise source comprises a gas delivery system.

21. A method according to claim 19, wherein the noise source comprises a motorized blower.

22. A method according to claim 19, wherein the noise control signals provide both noise cancellation and noise leveling functions, wherein noise leveling comprises leveling the perceived noise over a plurality of breath cycles.

23. A breathing assistance system having active noise control, the system comprising:
gas delivery means for supplying breathing gas;
patient interfacing means for interfacing with a patient for delivering breathing gas to one or more breathing passages of the patient;
gas communication means for communicating breathing gas supplied by the gas delivery means to the patient interfacing means for delivery to the patient; and
noise controlling means for controlling noise caused by a noise source associated with the breathing assistance system, the noise controlling means including:
  processing means for generating noise control signals for at least partially canceling noise caused by the noise source;
  control means for:
    generating noise source control signals for controlling the operation of the noise source; and
    communicating the noise source control signals to the processor;
  sound output means for outputting the noise control signals generated by the processor for at least partially canceling noise caused by the noise source; and
  feedback communication means for detecting noise caused by the noise source and noise control signals output by the speaker, and communicating to the processor feedback noise signals based on the detected noise;
wherein the processing means is configured to generate the noise control signals based at least on the noise source control signals from the control means and the feedback noise signals from the feedback communication means.

* * * * *